United States Patent
Kishimoto et al.

[11] Patent Number: 5,849,161
[45] Date of Patent: Dec. 15, 1998

[54] METHOD FOR TREATING SOLUTION OF ORGANIC COMPOUND

[75] Inventors: Hiroshi Kishimoto; Akira Omura, both of Okayama, Japan

[73] Assignee: Kuraray Co., Ltd., Japan

[21] Appl. No.: 820,173

[22] Filed: Mar. 19, 1997

[30] Foreign Application Priority Data

Mar. 29, 1996 [JP] Japan .................................. 8-077830

[51] Int. Cl.$^6$ ...................................................... B01D 3/38
[52] U.S. Cl. ........................... 203/96; 159/16.3; 159/47.1; 159/DIG. 10; 203/DIG. 21; 203/DIG. 23; 203/DIG. 25
[58] Field of Search ................................ 203/95, 96, 92, 203/DIG. 25, DIG. 21, DIG. 23; 568/913; 560/218; 159/16.3, DIG. 10, 47.1, 47.3; 210/702

[56] References Cited

U.S. PATENT DOCUMENTS

| | | | |
|---|---|---|---|
| 3,750,736 | 8/1973 | Batt et al. | 159/16.3 |
| 3,933,574 | 1/1976 | Zinoview et al. | 159/16.3 |
| 3,956,060 | 5/1976 | Scoggin | 203/96 |
| 3,968,003 | 7/1976 | Wolfe | 159/DIG. 10 |
| 4,347,098 | 8/1982 | Hubby | 159/16.3 |
| 4,432,837 | 2/1984 | Braun | 203/95 |
| 5,221,440 | 6/1993 | Miyagi et al. | 203/DIG. 25 |
| 5,430,127 | 7/1995 | Kelly | 528/500 |

FOREIGN PATENT DOCUMENTS

| | | |
|---|---|---|
| 52-012295 | 1/1977 | Japan . |
| 53-113880 | 10/1978 | Japan . |
| 54-090393 | 7/1979 | Japan . |
| 55-031471 | 3/1980 | Japan . |
| 0568452 | 8/1977 | U.S.S.R. ................ 159/16.3 |

*Primary Examiner*—Virginia Manoharan

[57] ABSTRACT

A solution of an organic compound containing at least a polymer is treated by adding an amount of water to said solution, distilling the organic compound to recover the organic compound, and incinerating the remained aqueous solution containing the polymer.

4 Claims, 1 Drawing Sheet

METHOD FOR TREATING SOLUTION OF ORGANIC COMPOUND

BACKGROUND OF THE INVENTION

1. Field of the Invention

The present invention relates to a method for treating a solution of an organic compound. In particular, the present invention relates to a method for treating a solution comprising an organic compound containing at least a polymer to recover the organic compound effectively and incinerating solids such as the polymer in the form of an aqueous solution.

2. Description of the Prior Art

Up to the present, chemical plants which treat organic compounds and polymers discharge a large amount of waste liquids comprising a mixture of such compounds and polymers, and a part of the waste liquid is recovered, while another part is incinerated.

For example, polyvinyl alcohol (PVA) is usually prepared by transesterifying polyvinyl acetate (PVAc) dissolved in methanol in the presence of a basic catalyst, and the obtained PVA is removed in the form of a solid, while methyl acetate as a by-product is recovered and reused in the form of acetic acid and methanol.

A waste liquid comprising primarily methanol contains solid components such as a minor amount of unreacted PVAc, PVA and sodium acetate ($CH_3COONa$) generated from the catalyst which are dissolved in the waste liquid. When the waste liquid containing these solids is treated in a recovering step, the solids have adverse effects on the recovering system such as clogging of pipes, heat-transfer pipes of heat exchangers, trays of distillation towers, and the like. To prevent such the adverse effects, the solids are removed from the waste liquid.

JP-A-54-90393 and JP-A-55-31471 disclose a method for removing a polymer which has been salted out with a filter as one method for removing the solid. JP-A-53-113880 and JP-A-52-12295 disclose a method for removing solid components in the solid form comprising concentrating a waste liquid with an evaporator to increase the solid content therein and evaporating the liquid from the concentrated waste liquid with a thin film evaporator, and the like.

However, salts remain in the solution in the method disclosed in JP-A-54-90393 and JP-A-55-31471, and scales cannot be completely prevented. In addition, the concentration of the salts in the waste water which is generated in the step for recovering the organic compound increases, and therefore the activity of an activated sludge deteriorates.

It is difficult to obtain the powder having stable properties such as shapes of the solids and remaining volatiles with the thin film evaporator by the method disclosed in JP-A-53-113880 and JP-A-52-12295, and the handling of the powder such as removal of the solid is very difficult. In particular, the handling is extremely difficult when the powder has strong adhesion and bridging properties.

It may be contemplated to incinerate the solids. However, the solids form clinkers in the incinerator when alkali metal salts are contained as the solids. Therefore, the solids cannot be stably burnt, and also the incinerator should be cleaned periodically.

SUMMARY OF THE INVENTION

One object of the present invention is to provide a method for effectively recovering an organic compound from a waste liquid.

Another object of the present invention is to provide method for recovering an organic compound from a waste liquid and, at the same time, removing a solid such as a polymer, an alkali metal salt, and the like in the form of an aqueous solution from the waste liquid and incinerating the aqueous solution without forming any clinker, which method can treat the solid in the liquid form without causing any environmental pollution.

According to the first aspect, the present invention provides a method for treating a solution which comprises an organic compound containing at least a polymer, comprising adding an amount of water to said solution and distilling said organic compound to recover said organic compound.

According to the second aspect, the present invention provides a method for treating a solution which comprises an organic compound containing at least a polymer, comprising adding an amount of water to said solution, distilling said organic compound to recover said organic compound, and incinerating the remained aqueous solution comprising said polymer.

BRIEF DESCRIPTION OF THE INVENTION

FIG. 1 is a flow chart for carrying out the method of the present invention in one embodiment.

DETAILED DESCRIPTION OF THE INVENTION

Figure 1:
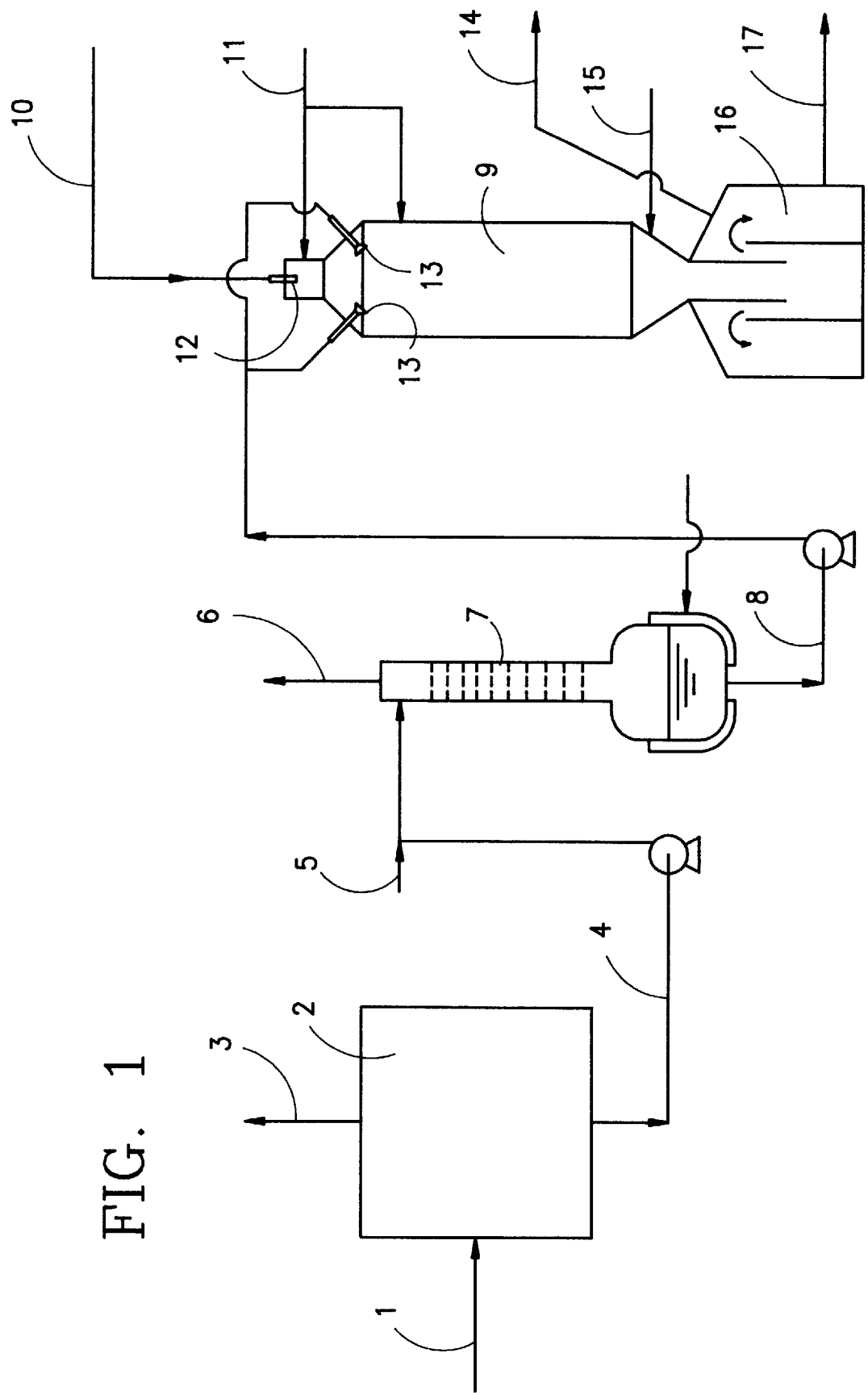

The solution which is treated by the method of the present invention comprises an organic compound which contains at least a polymer. Therefore, the solution may contain other material such as water in addition to the polymer and organic compound. The polymer is preferably a water-soluble polymer such as PVA in view of easy incineration.

The organic compound is distilled from the head of an distillation tower or evaporator. Therefore, the organic compound to be treated by the method of the present invention is one having a boiling point lower than that of water or one forming an azeotropic mixture with water having the lowest azeotropic point.

One of the most important characteristics of the present invention is the addition of water to the solution comprising an organic compound which contains at least a polymer. Thus, the organic compound is replaced with water and can be effectively recovered by distillation. At the same time, the polymer and the like are incinerated in the form of an aqueous solution. Therefore, they do not clog the supplying nozzle or nozzles for the incinerator and are stably incinerated. Accordingly, the waste water can be treated as one having the low COD.

The solution to be treated by the method of the present invention may contain an alkali metal salt such as $CH_3COONa$, etc.

The amount of water added to the solution is selected so that the weight ratio of water to the solid at the bottom of the distillation tower is in the range between 60:40 and 99:1, preferably between 90:10 and 95:5. When the amount of water is too large, the method becomes disadvantageous in view of the heat consumption, while when the amount of water is too small, the polymer and the like may be precipitated in the bottom of the distillation tower.

In the method of the present invention, an amount of water is added to the solution which comprises an organic compound containing at least a polymer before or when the solution is supplied into the distillation tower, and the organic compound is replaced with water. This replacement can decrease the amount of water to be entrained in the organic compound which will be recovered and also the amount of the organic compound mixed in the aqueous solution containing the solid which will be removed from the bottom. It is preferable to concentrate the solution to some extent, for example, from one tenth to one twentieth of the initial volume, with an evaporator prior to the treatment in the distillation tower so as to decrease the amount of added water.

The method of the present invention will be explained in detail by referring to the accompanying drawing.

A solution comprising an organic compound containing a polymer such as PVA, PVAc, etc., and an alkali metal salt such as $CH_3COONa$ is generated in the process for preparing PVA. Such the solution may be optionally concentrated with a conventional separating means such as a distillation tower, an evaporator, and the like. In FIG. 1, the solution is supplied into an evaporator 2 through a supply line 1.

When the evaporator is used, waste heat from other steps may be used as a heat source, but a multiple effect evaporator in which a steam from one evaporating unit is used for heating the subsequent one is thermally advantageous.

The preconcentrated solution is supplied into a distillation tower 7 through a line 4 for supplying a bottom liquid from the evaporator 2. At the same time, water is supplied into the tower 7 through a water-supply line 5. In FIG. 1, the evaporator has a line 3 for recovering an organic compound.

The solution to which water has been added is supplied into the top plate of the distillation tower 7.

The type of the distillation tower is not limited, but is usually a perforated plate tower, a bubble cap tower, and the like. Among them, the bubble cap tower is preferred in view of the resistance to scaling caused by the solids. The water content in the head fraction can be lowered by the provision of an enriching section in the distillation tower.

The heat source for the distillation tower can be a reboiler or direct blowing of steam.

Almost all the organic compound can be recovered together with added water from the tower head at a refluxing ratio of between 0 and 0.5. In some cases, the organic compound forms an azeotropic mixture with water. Almost all the organic compound is recovered through a line 6 for recovering the organic compound in FIG. 1.

The polymer and alkali metal salt in the form of an aqueous solution, that is, the aqueous solution of the solids, is drained from the bottom of the tower, and supplied to an incinerator 9 through a line 8.

The aqueous solution of the solids is incinerated. A submerged combustion incinerator is preferably used because of its high efficiency. The submerged combustion incinerator burns the aqueous solution of the solids by spraying the aqueous solution of the solids with a nozzle or nozzles into a flame generated with a burner from a fuel which can generate a high temperature flame such as heavy oil, kerosene, gas oil, etc., and bubbles the combustion gas directly through water to collect ashes in the combustion gas. An example of the submerged combustion incinerator is shown in FIG. 1. The incinerator comprises a burning furnace 9, a burner 12 to which a fuel and an air are supplied through a line 10 and a line 11, respectively, burners 13 for supplying a liquid to be burnt, a line 14 for exhausting gasses, a line 15 for supplying water, a submerged combusting can 16, and a drainage line 17.

The temperature in the incinerator is usually in the range between 800° and 1500° C.

When such the incinerator is used, the alkali metal salt is finely powdered and blown in water together with the combustion gas, and then dissolved in water. Therefore, the incinerator hardly suffers from troubles such as shut-down caused by the deposition of clinker-like scales in the inner wall of the incinerator, which is the problem associated with the burning of the solids. Since the solids are burnt in the form of an aqueous solution, the waste materials after burning the solids are removed in the form of an aqueous solution, and can be easily treated. In addition, the waste water is in the form of an aqueous solution of carbonates, and therefore the COD of the waste liquid is kept low. If the limited amount of the waste liquid is discarded, it does not worsen the environment.

The method of the present invention has been explained by making reference to the waste liquid from the process for producing polyvinyl alcohol, but it can be applied to any solution containing an organic compound containing a solid such as a polymer, an alkali metal salt, and the like.

EXAMPLES

The present invention will be explained by the following examples, which do not limit the scope of the present invention in any way.

Example 1

A waste liquid, which had been discharged from the PVA production process and contained 40 wt. % of methyl acetate, 58 wt. % of methanol, 1.5 wt. % of water, 0.25 wt. % of PVA and PVAc in total, and 0.25 wt. % of sodium acetate, was charged in an evaporator at a rate of 1000 kg/hr, and a fraction comprising primarily methyl acetate and methanol was distilled off. The waste liquid was concentrated to about one tenth of the initial volume, and the concentrated waste liquid contained 10 wt. % of methyl acetate, 80 wt. % of methanol, 5 wt. % of water, 2.5 wt. % of PVA and 2.5 wt. % of PVAc.

The concentrated waste liquid was supplied to the head of a bubble cap tower having a diameter of 350 mm and 8 plates at a rate of 105 kg/hr, while water was supplied to the head at a rate of 66 kg/hr. The tower was operated at the refluxing ratio of 0 (zero), and an aqueous solution containing methyl acetate and methanol was obtained from the head at a rate of 120 kg/hr.

An aqueous solution containing 10 wt. % of solids such as PVA, PVAc, sodium acetate, and the like was removed from the bottom of the tower at a rate of 51 kg/hr, and then supplied to an incinerator.

The incinerator was operated while supplying an air at a rate of 130 $Nm^3$/hr and maintaining the temperature at 950° C., but the nozzles were not clogged, and the incinerator was operated stably for a long time. The waste water containing sodium carbonate was obtained from the incinerator, and had COD of about 20 ppm. This waste water can be discharged as such.

After operating one year, the tower was disassembled, but little scales were found.

Example 2

A waste liquid containing 33.9 wt. % of methyl acetate, 64.9 wt. % of methanol, 0.9 wt. % of water, 0.16 wt. % of PVA and PVAc in total, and 0.16 wt. % of sodium acetate was charged in an evaporator at a rate of 1000 kg/hr and concentrated to about one fifteenth of the initial volume, and the concentrated waste liquid contained 7.2 wt. % of methyl acetate, 84.7 wt. % of methanol, 3.1 wt. % of water, 2.5 wt. % of PVA and PVAc, and 2.5 wt. % of sodium acetate.

The concentrated waste liquid was supplied to the head of a perforated plate tower having a diameter of 350 mm and 8 plates at a rate of 65 kg/hr, while water was supplied to the head at a rate of 68 kg/hr. The tower was operated at the refluxing ratio of 0 (zero), and an aqueous solution containing methyl acetate and methanol was obtained from the head at a rate of 69 kg/hr.

An aqueous solution containing 5 wt. % of solids such as PVA, PVAc, sodium acetate, and the like was removed from the bottom of the tower at a rate of 64 kg/hr, and then supplied to an incinerator.

The incinerator was operated while supplying an air at a rate of 200 Nm$^3$/hr and maintaining the temperature at 950° C., and the waste water having the COD of about 20 ppm was obtained from the incinerator. This waste water can be discharged as such.

After operating one year, the tower was disassembled, and scales were adhered slightly. The amount of consumed fuel was about 1.5 times larger than that in Example 1.

Example 3

The same concentrated waste liquid as obtained in Example 1 was supplied to the head of a perforated plate tower having a diameter of 350 mm and 8 plates at a rate of 105 kg/hr, while water was supplied to the head at a rate of 21 kg/hr. The tower was operated at the refluxing ratio of 0 (zero), and an aqueous solution containing methyl acetate and methanol was obtained from the head at a rate of 112 kg/hr.

An aqueous solution containing 35 wt. % of solids such as PVA, PVAc, sodium acetate, and the like was removed from the bottom of the tower at a rate of 14 kg/hr, and then supplied to an incinerator.

The incinerator was operated while supplying an air at a rate of 130 Nm$^3$/hr and maintaining the temperature at 950° C., and the waste water having COD of about 20 ppm was obtained from the incinerator. This waste water can be discharged as such.

The consumption of the fuel for the incineration was small, but a small amount of the solids were adhered to the nozzles of the incinerator.

Comparative Example 1

The same concentrated waste liquid as obtained in Example 1 was supplied to the head of a perforated plate tower having a diameter of 350 mm and 8 plates at a rate of 105 kg/hr, while water was supplied to the head at a rate of 17 kg/hr. The tower was operated at the refluxing ratio of 0 (zero), and an aqueous solution containing methyl acetate and methanol was obtained from the head at a rate of 110 kg/hr. However, the solids such as PVA, PVAc, sodium acetate and the like precipitated slightly in the aqueous solution from the bottom, and the solution could not be supplied to the incinerator.

Comparative Example 2

The same concentrated waste liquid as obtained in Example 1 was supplied at a rate of 40 liter/hr to a thin film evaporator having a heat transfer area of 0.14 m$^2$, and evaporated to dryness at 140° C., and a viscoelastic solid having irregular shapes and a particle size of between 10 and 20 mm was obtained.

This solid was stored in a hopper and discharging of the solid by an conveyor was tried. However, a mass of the solid was caught between the screw and the casing, and the screw stopped.

The particles stuck together and formed blocks at various parts in the hopper.

What is claimed is:

1. A method for treating a solution which comprises a water-soluble organic polymer and an organic compound selected from the group consisting of methyl acetate and methanol, said method comprising the steps of (a) supplying said solution and water to a distillation zone having a top region and a bottom region with the amount of water being selected so the weight ratio of water to solid at the bottom region is between 60:40 and 99:1, (b) carrying out distillation to distill off and recover the organic compound as an aqueous solution at the top region, (c) obtaining a waste product comprising an aqueous solution comprising said polymer at said bottom region and (d) incinerating the aqueous solution comprising said polymer.

2. A method according to claim 1, wherein the solution which is treated further comprises an alkali metal salt.

3. A method according to claim 2, wherein said alkali metal salt is a sodium acetate.

4. A method according to claim 1, wherein the solution which is treated is a waste liquid from a process for producing polyvinyl alcohol.

* * * * *

UNITED STATES PATENT AND TRADEMARK OFFICE
CERTIFICATE OF CORRECTION

PATENT NO. : 5,849,161
DATED : December 15, 1998
INVENTOR(S) : Hiroshi Kishimoto, et al.

It is certified that error appears in the above-identified patent and that said Letters Patent is hereby corrected as shown below:

On the title page, under "FOREIGN PATENT DOCUMENTS", insert:

--877360     9/61     United Kingdom--.

On the title page, under the listing of FOREIGN PATENT DOCUMENTS and above the Examiner's name and the ABSTRACT, insert:

--OTHER PUBLICATIONS

Patent Abstracts of Japan, Vol. 008, No. 283, C-258,
    12/84 (Abstract of JP 59 152336)
Patent Abstracts of Japan, Vol. 005, No. 054,
    C-050, 4/81 (Abstract of JP 56 007731)
Patent Abstracts of Japan, Vol. 004, No. 065,
    C-010, 5/80 (Abstract of JP 55 031471)
DATABASE WPI, Derwent Abstract of JP
    54 090 393 (Abstract XP-002066819), 7/79--.

Signed and Sealed this

Sixteenth Day of March, 1999

Attest:

Q. TODD DICKINSON

*Attesting Officer*      *Acting Commissioner of Patents and Trademarks*